US012766253B2

(12) United States Patent
Lehtinen et al.

(10) Patent No.: US 12,766,253 B2
(45) Date of Patent: Oct. 20, 2026

(54) AGENT ADMINISTERING MEDICAL DEVICE

(71) Applicant: Boston Scientific Scimed, Inc., Maple Grove, MN (US)

(72) Inventors: Laurie A. Lehtinen, Boylston, MA (US); Collin Murray, Maynard, MA (US); Gerald Fredrickson, Westford, MA (US); Ra Nam, Lawrence, MA (US); Daniel Congdon, Hudson, MA (US); Joseph Rausa, Littleton, MA (US); Andrew Pic, Northboro, MA (US); Tony Soukalopoulos, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 666 days.

(21) Appl. No.: 17/164,864

(22) Filed: Feb. 2, 2021

(65) Prior Publication Data

US 2021/0236723 A1 Aug. 5, 2021

Related U.S. Application Data

(60) Provisional application No. 62/969,888, filed on Feb. 4, 2020.

(51) Int. Cl.
*A61M 5/155* (2006.01)
*A61M 39/24* (2006.01)

(52) U.S. Cl.
CPC ............ *A61M 5/155* (2013.01); *A61M 39/24* (2013.01); *A61M 2039/248* (2013.01)

(58) Field of Classification Search
CPC .................. A61M 5/155; A61M 39/24; A61M 2039/248; A61M 13/00; A61M 2202/064;
(Continued)

(56) References Cited

U.S. PATENT DOCUMENTS

| | | | |
|---|---|---|---|
| 471,854 | A | 3/1892 | Howard |
| 881,238 | A | 3/1908 | Hasbrouck |
| 1,145,520 | A | 7/1915 | Smith |
| 1,599,959 | A | 9/1926 | Buheiji |
| 1,732,566 | A | 10/1929 | McKendrick |

(Continued)

FOREIGN PATENT DOCUMENTS

| | | | |
|---|---|---|---|
| CN | 101401956 | B | 11/2012 |
| DE | 60215438 | T2 | 8/2007 |
| EP | 3052168 | B1 | 11/2019 |
| JP | H07118305 | A | 5/1995 |
| WO | 03013552 | A1 | 2/2003 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Michael J Tsai
*Assistant Examiner* — Neeraja Gollamudi
(74) *Attorney, Agent, or Firm* — Bookoff McAndrews, PLLC

(57) ABSTRACT

A medical device that comprises an enclosure defining a cavity for containing an agent, a lumen for receiving a pressurized fluid, a channel between the cavity and the lumen, and a barrier positioned in the channel and defining a space, wherein in a first position of the barrier, the space is in fluid communication with the cavity to receive the agent from the cavity, and wherein the barrier is configured to rotate from the first position to a second position in which the space is in fluid communication with the lumen to deliver the agent from the space to the lumen.

20 Claims, 11 Drawing Sheets

(58) Field of Classification Search
CPC .......... A61M 11/02; A61M 2202/0225; A61M 2210/0625; A61M 2210/105; A61M 2210/1053; A61M 2210/1067; A61M 11/005; A61M 11/007; A61M 15/0036; A61M 15/0038; A61M 15/004; A61M 15/0085; A61M 15/0021; A61M 15/0041; A61M 15/005; A61M 15/0045; A61M 15/0048; A61B 2017/00367; A61B 2017/00407; A61B 2017/00539; A61B 2017/00544; A61B 2017/00685; A61B 2017/00818; A61B 17/00491
See application file for complete search history.

(56) References Cited

U.S. PATENT DOCUMENTS 2,151,418 A 3/1939 Bolté
2,185,927 A 1/1940 Shelanski
2,478,715 A 8/1949 Schmitt
2,623,519 A 12/1952 Cohen
3,669,113 A 6/1972 Altounyan et al.
3,940,061 A 2/1976 Gimple et al.
4,184,258 A 1/1980 Barrington et al.
4,427,450 A 1/1984 Kostansek
4,457,329 A 7/1984 Werley et al.
4,645,496 A * 2/1987 Oscarsson ............ A61B 5/0215 251/117
4,806,167 A 2/1989 Raythatha
5,046,528 A * 9/1991 Manska ................ F16K 31/602 251/304
5,215,221 A 6/1993 Dirksing
5,231,983 A 8/1993 Matson et al.
5,273,531 A 12/1993 Knoepfler
5,312,331 A 5/1994 Kneopfler
5,312,333 A 5/1994 Churinetz et al.
5,366,122 A 11/1994 Guentert et al.
5,445,612 A 8/1995 Terakura et al.
5,466,228 A * 11/1995 Evans ................. F16K 11/0853 604/32
5,470,311 A 11/1995 Setterstrom et al.
5,884,621 A 3/1999 Matsugi et al.
5,951,531 A 9/1999 Ferdman et al.
6,003,512 A 12/1999 Gerde
6,484,750 B1 11/2002 Foos et al.
6,554,022 B2 4/2003 Wakeman
6,589,087 B2 7/2003 Mackal et al.
6,684,917 B2 2/2004 Zhu et al.
6,708,712 B2 3/2004 Wakeman
6,716,190 B1 4/2004 Glines et al.
6,799,571 B1 10/2004 Hughes et al.
7,178,547 B2 2/2007 Mackal
7,311,270 B2 12/2007 Kapila
7,334,598 B1 2/2008 Hollars
7,361,300 B2 4/2008 Kelly et al.
7,427,607 B2 9/2008 Suzuki
7,455,248 B2 11/2008 Kablik et al.
7,461,649 B2 12/2008 Gamard et al.
7,544,177 B2 6/2009 Gertner
7,563,299 B2 7/2009 Baptista da Costa et al.
7,673,647 B2 3/2010 Mackal
7,841,338 B2 11/2010 Dunne et al.
7,892,205 B2 2/2011 Palasis et al.
7,921,874 B2 4/2011 Tekulve et al.
8,037,880 B2 10/2011 Zhu et al.
8,097,071 B2 1/2012 Burgess et al.
8,118,777 B2 2/2012 Ducharme et al.
8,269,058 B2 9/2012 McCarthy et al.
8,313,474 B2 11/2012 Campbell et al.
8,360,276 B2 1/2013 Rogier et al.
8,361,054 B2 1/2013 Ducharme et al.
8,496,189 B2 7/2013 Lomond et al.
8,673,065 B2 3/2014 Burgess et al.
8,721,582 B2 5/2014 Ji
8,728,032 B2 5/2014 Ducharme et al.
8,741,335 B2 6/2014 McCarthy
8,827,980 B2 9/2014 Ji
8,910,627 B2 12/2014 Iwatschenko et al.
8,951,565 B2 2/2015 McCarthy
9,028,437 B2 5/2015 Ott et al.
9,089,658 B2 7/2015 Dunne et al.
9,101,744 B2 8/2015 Ducharme
9,107,668 B2 8/2015 Melsheimer et al.
9,132,206 B2 9/2015 McCarthy
9,204,957 B2 12/2015 Gregory et al.
9,205,170 B2 12/2015 Lucchesi et al.
9,205,207 B2 12/2015 Ji
9,205,240 B2 12/2015 Greenhalgh et al.
9,308,584 B2 4/2016 Burgess et al.
9,310,812 B2 4/2016 Costle et al.
9,375,533 B2 6/2016 Ducharme et al.
9,492,646 B2 11/2016 Hoogenakker et al.
9,517,976 B2 12/2016 Mackal
9,545,490 B2 1/2017 Iwatschenko et al.
9,555,185 B2 1/2017 Foster et al.
9,629,966 B2 4/2017 Ji
9,636,470 B2 5/2017 Pohlmann et al.
9,707,359 B2 7/2017 Kubo
9,713,682 B2 7/2017 Eistetter et al.
9,717,897 B2 8/2017 Rogier
9,821,084 B2 11/2017 Diegelmann et al.
9,839,772 B2 12/2017 Ducharme
9,839,774 B2 12/2017 Bonaldo
9,846,439 B2 12/2017 Carman et al.
9,867,931 B2 1/2018 Gittard
9,976,660 B2 5/2018 Stanton et al.
10,004,690 B2 6/2018 Lee et al.
10,010,705 B2 7/2018 Greenhalgh et al.
10,017,231 B2 7/2018 Fawcett, Jr.
10,036,617 B2 7/2018 Mackal
10,065,004 B2 9/2018 Eder et al.
10,173,019 B2 1/2019 Kaufmann et al.
10,384,049 B2 8/2019 Stanton et al.
10,463,811 B2 11/2019 Lee et al.
10,507,293 B2 12/2019 Goodman et al.
10,646,706 B2 5/2020 Rogier
10,730,595 B2 8/2020 Fawcett
10,751,523 B2 8/2020 Rogier
10,806,853 B2 10/2020 Gittard
10,850,814 B2 12/2020 Fawcett
10,994,818 B2 5/2021 Hernandez
2003/0125674 A1 * 7/2003 Cise ...................... A61M 39/24 604/247
2004/0107963 A1 * 6/2004 Finlay ............... A61M 15/0021 128/203.15
2004/0249359 A1 12/2004 Palasis et al.
2005/0121025 A1 6/2005 Gamard et al.
2005/0147656 A1 7/2005 McCarthy et al.
2005/0220721 A1 10/2005 Kablik et al.
2006/0004314 A1 1/2006 McCarthy et al.
2006/0213514 A1 9/2006 Price et al.
2007/0056586 A1 3/2007 Price et al.
2007/0066920 A1 3/2007 Hopman et al.
2007/0066924 A1 3/2007 Hopman et al.
2007/0082023 A1 4/2007 Hopman et al.
2007/0083137 A1 4/2007 Hopman et al.
2007/0125375 A1 6/2007 Finlay et al.
2007/0151560 A1 7/2007 Price et al.
2007/0199824 A1 8/2007 Hoerr et al.
2008/0021374 A1 1/2008 Kawata
2008/0058720 A1 * 3/2008 Spohn ................... A61M 39/24 137/7
2008/0287907 A1 11/2008 Gregory et al.
2009/0101144 A1 4/2009 Gamard et al.
2009/0155342 A1 6/2009 Diegemann et al.
2009/0281486 A1 11/2009 Ducharme
2010/0121261 A1 5/2010 Kablik et al.
2010/0305505 A1 12/2010 Ducharme et al.
2011/0073200 A1 3/2011 Overvaag et al.
2011/0274726 A1 11/2011 Guo et al.
2011/0308516 A1 12/2011 Price et al.
2014/0271491 A1 9/2014 Gittard et al.
2015/0051536 A1 * 2/2015 Mendels ............. A61M 1/3659 604/246

(56) References Cited

U.S. PATENT DOCUMENTS

| | | | | |
|---|---|---|---|---|
| 2015/0094649 | A1 | 4/2015 | Gittard | |
| 2015/0125513 | A1 | 5/2015 | McCarthy | |
| 2016/0074579 | A1* | 3/2016 | Ilan | A61M 5/162 604/24 |
| 2016/0375202 | A1 | 12/2016 | Goodman et al. | |
| 2017/0106181 | A1 | 4/2017 | Bonaldo et al. | |
| 2017/0232141 | A1 | 8/2017 | Surti et al. | |
| 2017/0252479 | A1 | 9/2017 | Ji et al. | |
| 2017/0296760 | A1 | 10/2017 | Lee et al. | |
| 2018/0099088 | A1 | 4/2018 | Gittard | |
| 2018/0193574 | A1* | 7/2018 | Smith | A61M 13/00 |
| 2018/0214160 | A1 | 8/2018 | Hoskins et al. | |
| 2018/0339144 | A1 | 11/2018 | Greenhalgh et al. | |
| 2019/0134366 | A1 | 5/2019 | Erez et al. | |
| 2019/0217315 | A1 | 7/2019 | Maguire et al. | |
| 2019/0232030 | A1* | 8/2019 | Pic | A61B 17/00491 |
| 2021/0024187 | A1 | 1/2021 | Fawcett et al. | |
| 2021/0069485 | A1 | 3/2021 | Rogier | |

FOREIGN PATENT DOCUMENTS

| | | | | |
|---|---|---|---|---|
| WO | 2004066806 | A2 | 8/2004 | |
| WO | 2005062896 | A2 | 7/2005 | |
| WO | 2006071649 | A2 | 7/2006 | |
| WO | 2006088912 | A2 | 8/2006 | |
| WO | WO-2007015665 | A1 * | 2/2007 | A61M 15/0065 |
| WO | 2008033462 | A2 | 3/2008 | |
| WO | 2009061409 | A1 | 5/2009 | |
| WO | 2015050814 | A1 | 4/2015 | |
| WO | 2018157772 | A1 | 9/2018 | |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

Retsch GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

* cited by examiner

AGENT ADMINISTERING MEDICAL DEVICE

CROSS-REFERENCE TO RELATED APPLICATIONS

This application claims the benefit of priority from U.S. Provisional Application No. 62/969,888, filed on Feb. 4, 2020, which is incorporated by reference herein in its entirety.

TECHNICAL FIELD

This disclosure relates generally to a medical device that administers an agent. More particularly, at least some embodiments of the disclosure relate to a medical device including a system that administers a dosage of an agent to a lumen via, for example, a rotatable mechanism.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. This disclosure may solve one or more of these issues or other issues in the art.

SUMMARY OF THE DISCLOSURE

According to an example, a medical device may comprise an enclosure defining a cavity for containing an agent, a lumen for receiving a pressurized fluid, a channel between the cavity and the lumen, and a barrier positioned in the channel and defining a space. In a first position of the barrier, the space may be in fluid communication with the cavity to receive the agent from the cavity. The barrier may be configured to rotate from the first position to a second position in which the space may be in fluid communication with the lumen to deliver the agent from the space to the lumen.

In another example, the space may be a first space of a plurality of spaces of the barrier, and wherein in the first position of the barrier, the first space may be in fluid communication with the lumen to deliver the agent from the first space, and a second space of the plurality of spaces may be in fluid communication with the cavity to receive the agent. The barrier may seal the cavity from the lumen, inhibiting the pressurized fluid of the lumen from entering into the cavity.

In another example, a medical device may further comprise at least one seal defining at least a portion of the channel, wherein the at least one seal contacts the barrier to inhibit the agent from entering the lumen without entering the space, and to inhibit the agent from exiting the space prior to the barrier being in the second position.

In another example, a medical device may further comprise a second channel between the cavity and the lumen. A medical device may further comprise a second barrier positioned in the second channel and defining a second barrier space, wherein in a first position of the second barrier, the second barrier space is in fluid communication with the cavity to receive the agent from the cavity, and wherein the second barrier is configured to rotate from the first position to a second position in which the second barrier space is in fluid communication with the lumen to deliver the agent from the second barrier space to the lumen.

According to another example, a medical device may further comprise a turbine positioned within the lumen so that the pressurized fluid rotates the turbine, and rotation of the turbine rotates the barrier from the first position to the second position.

In another example, the barrier may be a wheel, wherein the wheel includes an axis and a plurality of paddles extending from the axis, and wherein a gap between adjacent paddles defines the space. In another example, the barrier may be an auger, and wherein a gap between adjacent blades of the auger defines the space.

In another example, the barrier may be a ball valve, wherein the ball valve includes at least one pair of prongs and a gap between the prongs defines the space. The at least one pair of prongs may include a first and second pairs of prongs diametrically opposed across the ball valve, and the gap between the prongs in the first pair of prongs defines a first space, and the gap between the prongs in the second pair of prongs defines a second space.

According to an example, a rotation of the barrier may be actuated by a mechanical system or a hydraulic system associated with the medical device. The lumen may be a flexible catheter capable of traversing a tortuous body lumen, and further comprising a source of the pressurized fluid. The barrier may be configured to rotate from the first position to a second position via both clockwise rotation and counterclockwise rotation. The barrier may be configured to rotate at least one of 90° or 180°, to transition from the first position to the second position.

In another example, a medical device may comprise an enclosure defining a cavity for containing the agent, a lumen for receiving a pressurized fluid, and a barrier defining a space and positioned to inhibit fluid communication between the cavity and the lumen. In a first position of the barrier, the space may be in fluid communication with the cavity to receive the agent from the cavity, and the barrier may configured to rotate from the first position to a second position in which the space is in fluid communication with the lumen to deliver the agent from the space to the lumen. The barrier may be a ball valve, and the ball valve may include at least one pair of prongs and a gap between the prongs defines the space. The ball valve may be positioned in the lumen below the cavity, and the ball valve may be configured to rotate counterclockwise to rotate from the first position to the second position. The barrier may be configured to rotate 90° to transition from the first position to the second position.

According to an example, a method of administering an agent via a medical device, the medical device including a lumen, an enclosure defining a cavity containing the agent, and a barrier within a channel between the cavity and the lumen, the method may include: positioning a distal end of the lumen adjacent to a target site, wherein the barrier defines a space that receives and stores the agent from the cavity, providing a pressurized fluid to the lumen, and rotating the barrier relative to the lumen so that fluid communication is established between the space and the lumen to deliver the agent from the space to the lumen.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of the disclosure may solve one or more of the limitations in the art. The scope of the disclosure, however, is defined by the attached claims and not the ability to solve a specific problem. The disclosure is drawn to medical devices configured to administer doses of agents, e.g., therapeutic agents, among other aspects. The agent may be in any suitable form, including a powder form, which may be delivered to a stream of propellant/pressurized fluid, e.g., $CO_2$, nitrogen, air, or other liquids, etc. Said medical devices allow for the administration of agents in metered doses, which allows for a greater consistency in the quantity of the agent that reaches a target site.

Figure 1A:
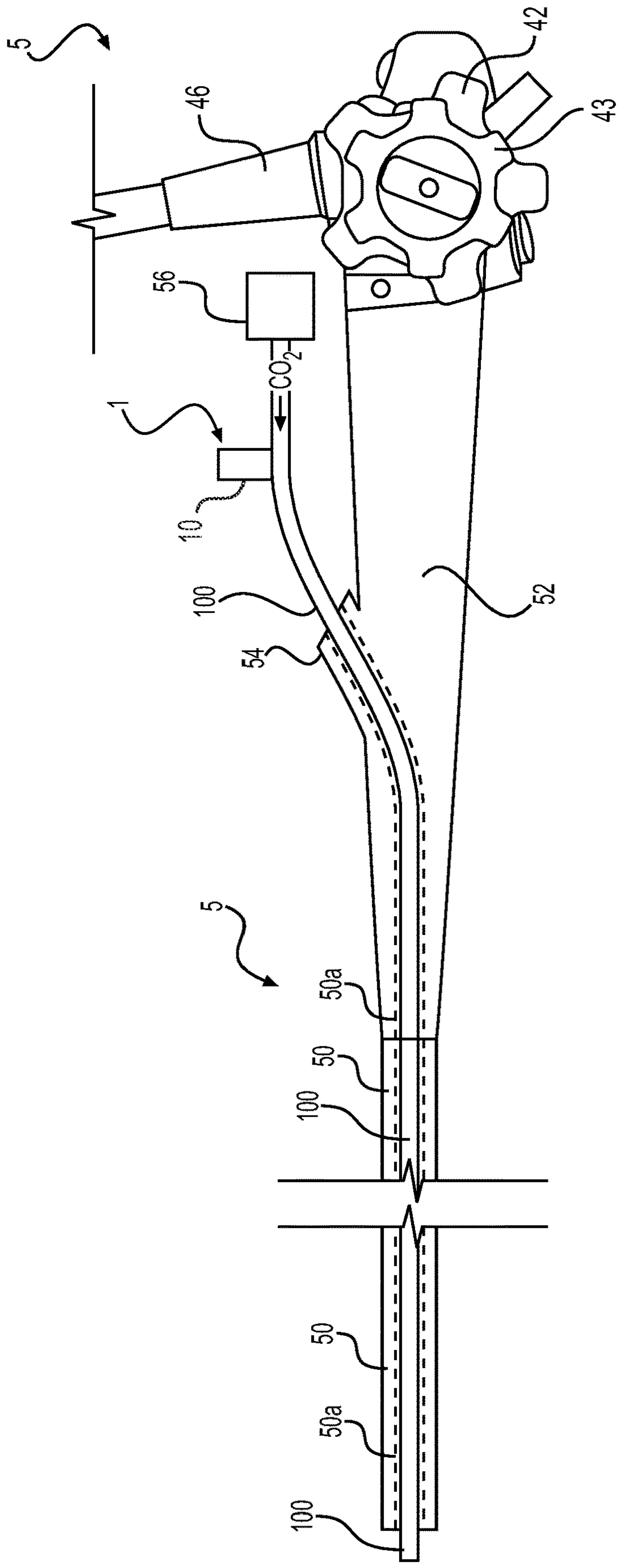
FIG. 1A is a side view of a portion of a shaft of an endoscope including a medical device, according to an embodiment.

Referring to FIG. 1A, a medical system 5, e.g., including an endoscope, according to an embodiment is shown. Medical system 5 includes a flexible shaft 50 (e.g., a catheter) and a handle 52 connected at a proximal end of flexible shaft 50. Handle 52, or some other device for actuating or controlling medical system 5 and any tool or devices associated with medical system 5, includes first and second actuating devices 42, 43, which control articulation of flexible shaft 50, and/or an articulation joint at a distal end of flexible shaft 50, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of medical system 5 and connect to flexible shaft 50 to control movement thereof. Alternatively, or additionally, a user may operate actuating elements independently of handle 52. Distal ends of actuating elements may extend through flexible shaft 50 and terminate at an articulation joint and/or a distal tip of flexible shaft 50. For example, one or more actuating elements may be connected to an articulation joint, and actuation of actuating elements may control the articulation joint or the distal end of flexible shaft 50 to move in multiple directions.

In addition, one or more electrical cables (not shown) may extend from the proximal end of endoscope 5 to the distal end of flexible shaft 50 and may provide electrical controls to imaging, lighting, and/or other electrical devices at the distal end of flexible shaft 50, and may carry imaging signals from the distal end of flexible shaft 50 proximally to be processed and/or displayed on a display. Handle 52 may also include ports 54, 46 for introducing and/or removing tools, fluids, or other materials from the patient. Port 54 may be used to introduce tools. Port 46 may be connected to an umbilicus for introducing fluid, suction, and/or wiring for electronic components. For example, as shown in FIG. 1A, port 54 receives a tube 100, which extends from the proximal end to the distal end of flexible shaft 50, via a working channel 50*a* of shaft 50.

As shown in FIG. 1A, tube 100 of medical device 1 is attached to a pressurized fluid source 56, e.g., $CO_2$, which may be controlled by a user to turn on/off and to adjust a rate at which fluid flows into tube 100. Source 56 may be a fluid canister or tank, a source of fluid supplied by a medical facility, or any other suitable source. Medical device 1 further includes an enclosure 10. A channel 12 (FIG. 1B) is positioned between enclosure 10 and tube 100. Enclosure 10 and channel 12 are coupled to a proximal portion of tube 100, distal of the connection between tube 100 and source 56.

Figure 1B:
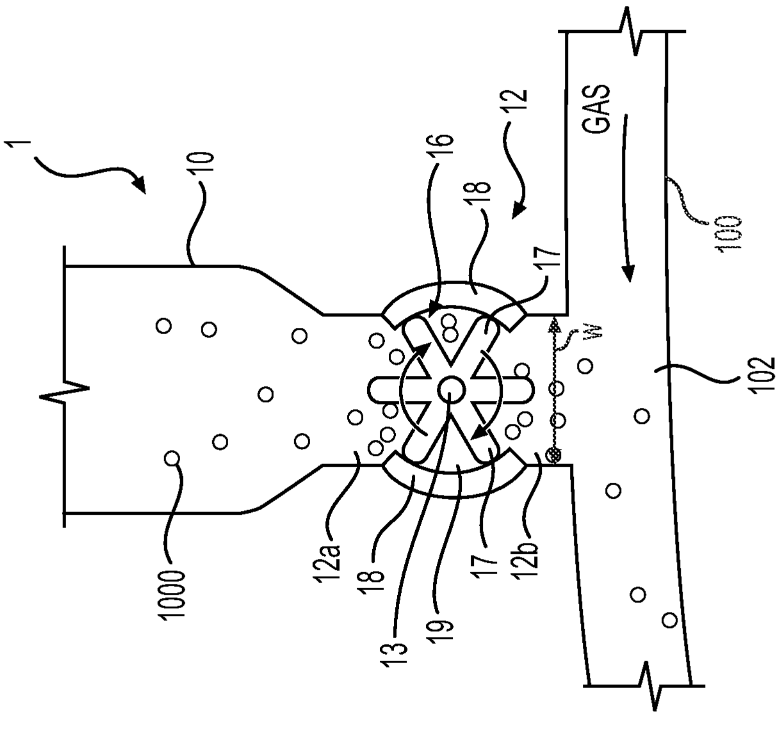
FIG. 1B is a cross-sectional view of a portion of the medical device of FIG. 1A.

FIG. 1B illustrates an embodiment of a portion of medical device 1 in FIG. 1A in further detail. As discussed above, medical device 1 includes enclosure 10 defining a cavity for containing an agent 1000, a tube (e.g., a catheter or a sheath) 100 defining a lumen 102 receiving pressurized fluid, e.g., $CO_2$, from a proximal end, and a channel 12 positioned between the cavity of enclosure 10 and lumen 102. The shape or size of enclosure 10 is not particularly limited, and may be any suitable shape or size for storing an amount of agent 1000. In medical device 1, a bottom portion of enclosure 10 tapers into channel 12. Channel 12 extends from the bottom of enclosure 10 to lumen 102, thereby providing a passage for agent 1000 to travel from channel 12 to lumen 102. Channel 12 is of a smaller width, diameter, and/or cross-sectional area than that of enclosure 10. However, the shape and dimensions of channel 12 is not particularly limited. Channel 12 includes a metering wheel 16 and seals 18 partially surrounding wheel 16.

Figure 1C:
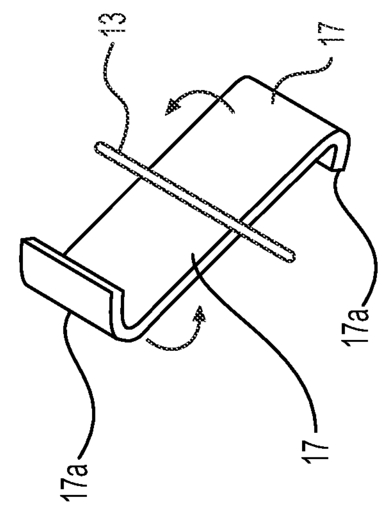
FIG. 1C is a perspective view of a portion of a wheel of the medical device of FIG. 1A.
Figure 1D:
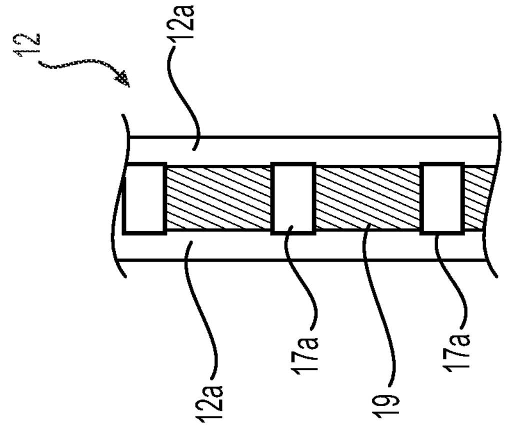
FIG. 1D is a side view of a portion of the medical device of FIG. 1A.

Wheel 16 is positioned between a first end 12*a* and a second end 12*b* of channel 12, and is oriented so that the rotational axis 13 of wheel 16 is perpendicular or substantially perpendicular to the width w of channel 12. Wheel 16 may be rotatable in a clockwise or a counter-clockwise direction. Wheel 16 includes six spokes 17, all of which extend radially outward from axis 13. Spokes 17 are paddle-like and rectangular in shape, as shown in FIG. 1C. Spokes 17 are of a length that is equal to or about equal to the distance from axis 13 to curved seals 18. Thus, spokes 17 are of a length so that radially outward ends of spokes 17 are in constant or near constant contact with seals 18 (except when said spokes 17 are directed towards end 12*a* or end 12*b*, between seals 18). Such contact prevents, agent 1000 from falling unimpeded through channel 12 to lumen 102 from enclosure 10. Furthermore, such contact inhibits the air/pressurized fluid from lumen 102 from entering into enclosure 10 and reaching agent 1000. Thus, agent 1000 of enclosure 10 is protected and sealed from the pressurized fluid source from lumen 102. Spokes 17 may be of any suitable material, e.g., rubber, that may help provide a proper seal along the edges of seals 18 and also inhibit adherence of agent 1000 to spokes 17. Spokes 17 may additionally include flanges 17*a*, as shown in FIGS. 1C-1D, on the ends adjacent to seals 18 to further facilitate sealing with seals 18. In this instance, however, wheel 16 would preferably rotate counter-clockwise so that the protruding ends of flanges 17*a* do not catch against the ends and/or surfaces of seals 18, thereby inhibiting rotation of wheel 16. Furthermore, FIG. 1C shows that, in some embodiments, diametrically opposed spokes 17 of wheel 16 are of a single, monolithic piece with rotational axis 13 coupled to a midpoint of the piece. Axis 13 is coupled along the width of said piece to form two spokes 17 that are equal in length. FIG. 1D shows a cross-sectional view of a portion of the side of channel 12. As shown, spokes 17 (not shown due to flanges 17*a*) and flanges 17*a* are evenly spaced apart to form buckets 19 of equal size. Furthermore, there is tight tolerance between walls 12*a* of channel 12 and flanges 17*a*, such that flanges 17*a* and walls 12*a* are in contact, or in near contact with one another. This further seals enclosure 10 from the air/fluid supplied to lumen 102, and lumen 102 from agent 1000 disposed in enclosure 10.

Spokes 17 are evenly distributed about axis 13 so that equal spaces, or buckets 19, are formed between spokes 17. Buckets 19 are configured to receive and store amounts of agent 1000 from enclosure 10. As empty buckets 19 are rotated underneath enclosure 10, agent feeds 1000 into buckets 19 via gravity or any suitable means. Furthermore, buckets 19 dispense agent 1000 as loaded buckets 19 are rotated, via rotation of wheel 16, to face and empty agent 1000 into lumen 102, again due to gravity or any suitable means. Buckets 19 may be sized so that a number of buckets 19, e.g., one, is of an appropriate size to contain a desired dosage of agent 1000. For example, an appropriate dose may be between about 0.1 to 1 g of agent 1000, for every second of fluid (e.g., gas) delivery in lumen 102.

Each seal 18 has a curved radially-inward, concave surface to accommodate for spokes 17. Seals 18 are positioned to partially surround wheel 16 and to provide a seal between first end 12*a* and second end 12*b* of channel 12. Thus, seals 18 inhibit agent 1000 from falling into lumen 102 without passing through wheel 16, and also inhibit agent 1000 from spilling out of buckets 19 prior to the intended agent-dispensing period. Furthermore, seals 18 also help inhibit air/pressurized fluid from entering into enclosure 10 and reaching agent 1000. Seals 18 may be of any suitable materials, e.g., silicon rubber, to provide a suitable seal with spokes 17.

Figure 1E:
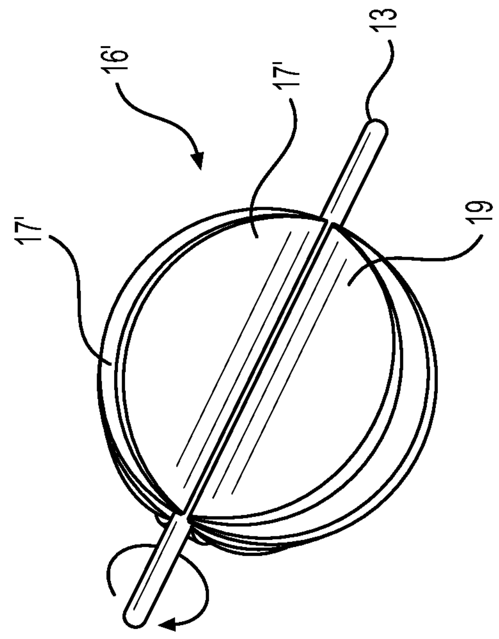
FIG. 1E is a perspective view of the wheel of a portion of a medical device, according to another embodiment.

It is noted that the metering mechanism of medical device 1 is not limited to wheel 16. Any suitable, rotatable mechanism may be used to receive and dispense a dose of agent 1000. For example, a spherical wheel 16', as shown in FIG. 1E, may be used as the metering mechanism, in place of wheel 16, within channel 12. Wheel 16' includes a plurality of paddles 17', e.g., six, extending from axis 13. Each paddle 17' is partially-circular (e.g., a half-circle) or dome-shaped. Paddles 17' collectively outline a sphere. To form such a shape, paddles 17' may be formed from a plurality of monolithic, circular or disk-shaped pieces with axis 13 coupled to midpoints of the pieces along the diameters of said pieces. Thus, a single monolithic circular piece may form two paddles 17' of equal size and shape that are diametrically opposed to one another. Moreover, like spokes 17, paddles 17' may be spaced apart evenly about axis 13 to form buckets 19 of equal sizes between adjacent paddles 17'. Thus, wheel 16' may function in the same manner as wheel 16, and may also be surrounded by seals 18.

Figure 5:
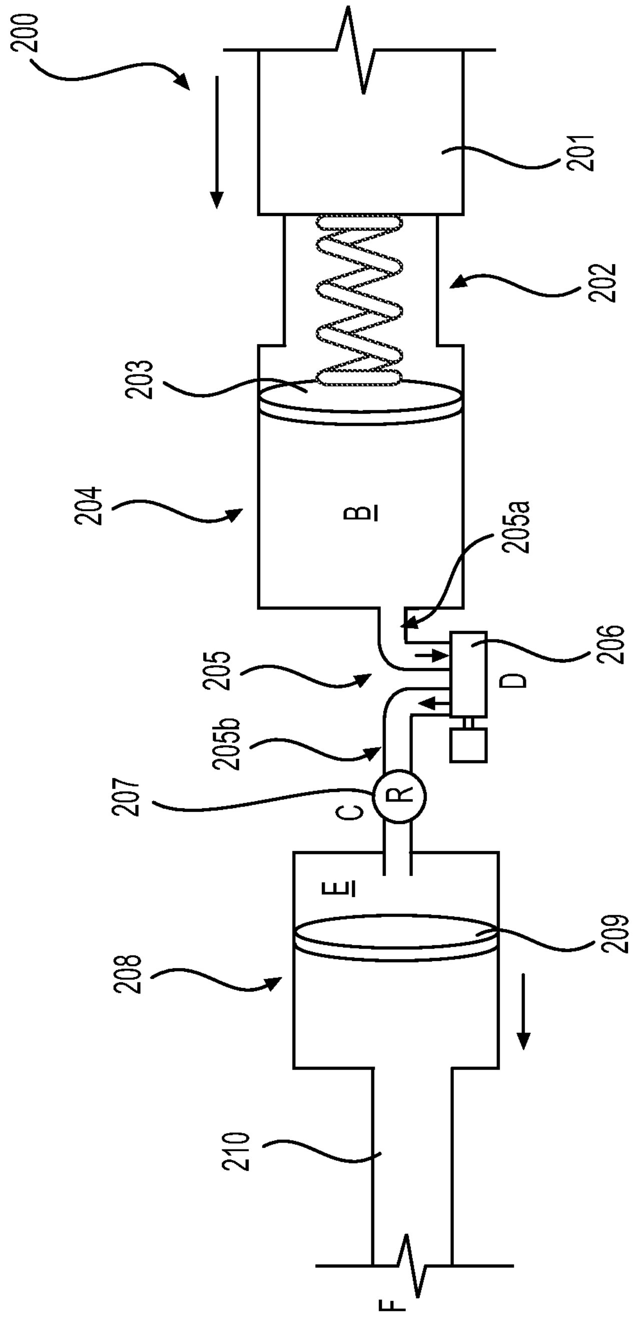
FIG. 5 is a cross-sectional view of a hydraulic mechanism, according to an embodiment.

Wheel 16 may be rotated via any suitable mechanism, e.g., gearing actuated by a mechanical trigger, liquid-pushed hydraulic, spring compression/winding, motor, etc., and is not particularly limited. For example, in some embodiments, axis 13, about which wheel 16 rotates, may be coupled to a gear (not shown), which may be connected to a geared lever (not shown). Such a geared lever may be actuated, e.g., pulled, to rotate the gear of axis 13, thereby rotating wheel 16. Actuation of a trigger/lever may result in a continuous rotation of wheel 16, or a consistent degree of rotation per actuation, e.g., a pull. A similar gearing mechanism is further discussed below, when referring to FIG. 3B, and may be used to rotate wheel 16. In some other embodiments, axis 13 may be coupled to a hydraulic system via any suitable means, so that said hydraulic system may actuate rotation of wheel 16 about axis 13, thereby dispensing agent 1000. This may also result in a continuous delivery of agent 1000, per a cycle of the hydraulic system. An example of a hydraulic system 200 is shown in FIG. 5, which is described in further detail below.

Referring to FIG. 1B, an example of how medical device 1 may be used is further discussed below. A user may deliver a distal end of tube 100 of medical device 1 into the body of a subject, e.g., via a natural orifice (such as a mouth or anus) and through a tortuous natural body lumen of the subject, such as an esophagus, stomach, colon, etc. Tube 100 may be delivered in any suitable way, for example, through working channel 50*a* of endoscope 5, by inserting a distal end of tube 100 into port 54 of endoscope 5. A user may direct/position the distal end of tube 100 to an intended target site for administration of agent 1000. A user may then fill enclosure 10 with agent 1000, if not filled already. A user may then rotate wheel 16 by any suitable actuating mechanism that is incorporated with medical device 1, e.g., geared lever/trigger, hydraulic, spring compression/winding, motor, thereby filling one or more buckets 19 with agent 1000 and administering a metered dose of agent 1000 to lumen 102. A user may turn on the pressurized fluid source at any suitable time to supply pressurized fluid until the metered dose of agent 1000 reaches the target tissue site. Alternatively, a user may start supply of pressurized fluid after the supply of agent 1000 to lumen 102. For example, a user may supply agent 1000 to lumen 102, supply pressurized fluid to lumen 102 to propel the supplied agent 1000 towards the distal end of lumen 102, and then repeat the aforementioned steps. In other examples, a user may engage an actuation mechanism that simultaneously rotates wheel 16 and also turns on the pressurized fluid source to flow pressurized fluid through lumen 100.

Figure 2A:
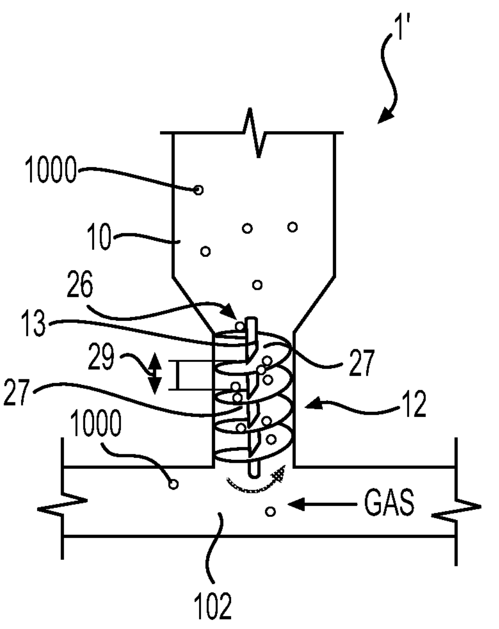
FIG. 2A is a cross-sectional view of a medical device, according to another embodiment.

Medical device 1', as shown in FIG. 2A, is similar to device 1 in many respects. Like reference numerals refer to like parts. Differences between device 1 and device 1' will be described below. Device 1' includes a rotatable auger 26 within a cylindrical or tubular channel 12 as the metering mechanism, instead of wheel 16 of device 1. Auger 26 is positioned vertically within channel 12 so that rotational axis 13 is aligned with the central axis of channel 12. Auger 26 includes a spirally arranged blade 27 that coils around rotational axis 13 from top to bottom. Furthermore, the diameter of auger 26 may be equal to or around the width between the inner surface of tubular channel 12. As a result, blade 27 juts radially outward from axis 13 by a distance so that blade 27 is in constant contact with the inner surface of channel 12. Thus, blade 27 may prevent agent 1000 from falling into lumen 102 unimpeded, without passing through auger 26. Furthermore, blade 27 also inhibits the air/pressurized fluid from lumen 102 from entering into enclosure 10.

The coiling/spiraling and pitch of blade 27 is such that the spacing between each coil is equal or approximately equal so that an even, consistent section 29 is formed throughout auger 26, between said adjacent coils of blade 27. It is noted that section 29 is a fluid channel that runs spirally downwards between two adjacent coils of blade 27. Section 29 is configured to receive and store amounts of agent 1000 from enclosure 10, which may be mechanically or gravity-fed to auger 26. The rotation of auger 16 may spirally descend agent 1000, held within section 29, and dispense agent 1000 into lumen 102. The width of section 29, e.g., the distance or pitch between adjacent coils of blade 27, may be such that said width, along with the rate of rotation, may dispense a desired dosage of agent 1000. Furthermore, the dimension of section 29 and the rate of rotation may be tailored to meet a predetermined or selected dose range. For example, an appropriate dose range may be between about 0.1 to 1 g of agent 1000, for every second of fluid delivery in lumen 102.

Figure 2B:
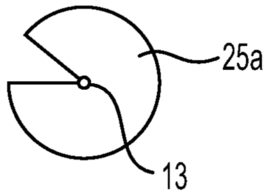
FIGS. 2B-2C are views of the top and the bottom of the auger of the medical device of FIG. 2A.
Figure 2C:
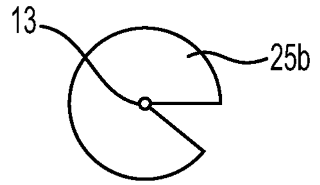

FIGS. 2B-2C show a top barrier 25*a* and a bottom barrier 25*b* that may be implemented within channel 12, respectively at a top and a bottom of channel 12 (not shown in FIG. 2A). Top barrier 25*a*, shown in FIG. 2B, may be a flat barrier that is placed above auger 26 at about the entrance of channel 12. Top barrier 25*a* may be coupled to axis 13 at its center point, and barrier 25*a* includes an opening leading to channel 12 and auger 26. Said opening is equal to or about equal to a sector that is one-eighth of the area of the opening of channel 12. In other embodiments, top barrier 25*a* may not be coupled to axis 13 and instead may be fixed to the walls of channel 12. In such embodiments, top barrier 25*a* will not rotate with auger 26. Bottom barrier 25*b*, shown in FIG. 2C, may be below auger 26 at about the end/exit of channel 12. Bottom barrier 25*b* may also be coupled to axis 13 at its center point. Barrier 25*b* includes an opening leading to lumen 102. The opening of barrier 25*b* may be the same size or about a similar size as that of barrier 25*a*. In other embodiments, bottom barrier 25*b* may not be coupled to axis 13 and instead may be fixed to the walls of channel 12, so that barrier 25*b* will not rotate with auger 26. Top barrier 25*a* and bottom barrier 25*b* may be oriented relative to one another such that their respective openings mirror one another and do not overlie one another. Thus, top barrier 25*a* is open where bottom barrier 25*b* is closed, and vice versa. Top barrier 25*a* and bottom barrier 25*b* may not only control the amount of agent 1000 entering and exiting channel 12, but also help sequester agent 1000 in enclosure 10 from the fluid stream in lumen 102.

Like wheel 16 of medical device 1, auger 26 may be rotated via any suitable mechanism, e.g., gearing actuated by a mechanical trigger, liquid-pushed hydraulic, spring compression/winding, motor, etc., and is not particularly limited. Thus, medical device 1' may be used in a similar manner as medical device 1, except a user rotates auger 26.

Figure 2D:
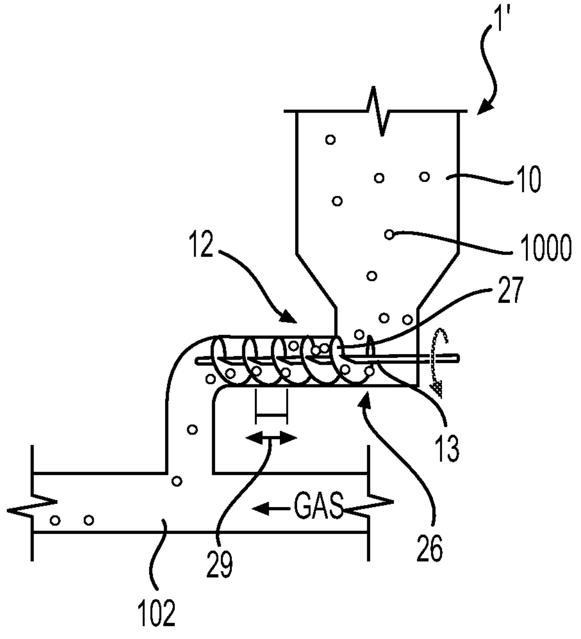
FIG. 2D is a cross-sectional view of a portion of a medical device, according to another embodiment.

FIG. 2D illustrates an example of an alternative configuration of medical device 1'. In this configuration, a proximal portion of channel 12 and auger 26 are positioned horizontally, relative to enclosure 10. From its initial horizontal orientation, a distal portion of channel 12 curves downward to fluidly connect to lumen 100, thereby allowing agent 1000 to fall downward towards lumen 100. Auger 26 is also parallel, or about parallel, to lumen 100. Furthermore, blade 27 juts radially outward by a distance so that blade 27 is in contact with the inner surface of channel 12. However, apart from the previously described structural differences, the configuration of medical device 1' shown in FIG. 2B operates in the same manner as the configuration illustrated in FIG. 2A.

Figure 3B:
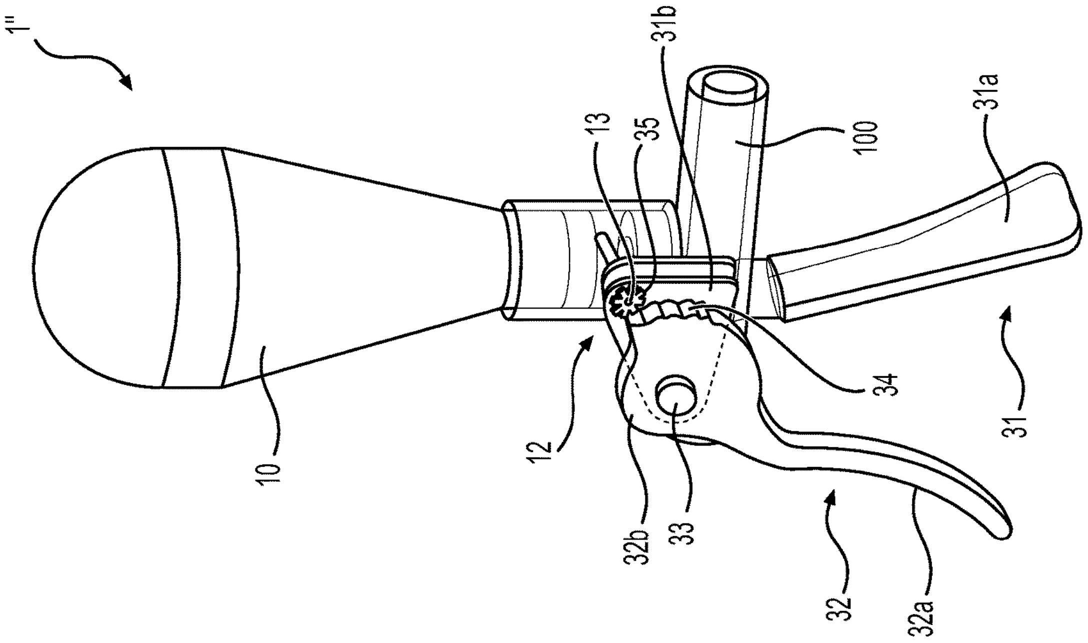
FIG. 3B is a perspective view of the medical device of FIG. 3A.
Figure 3A:
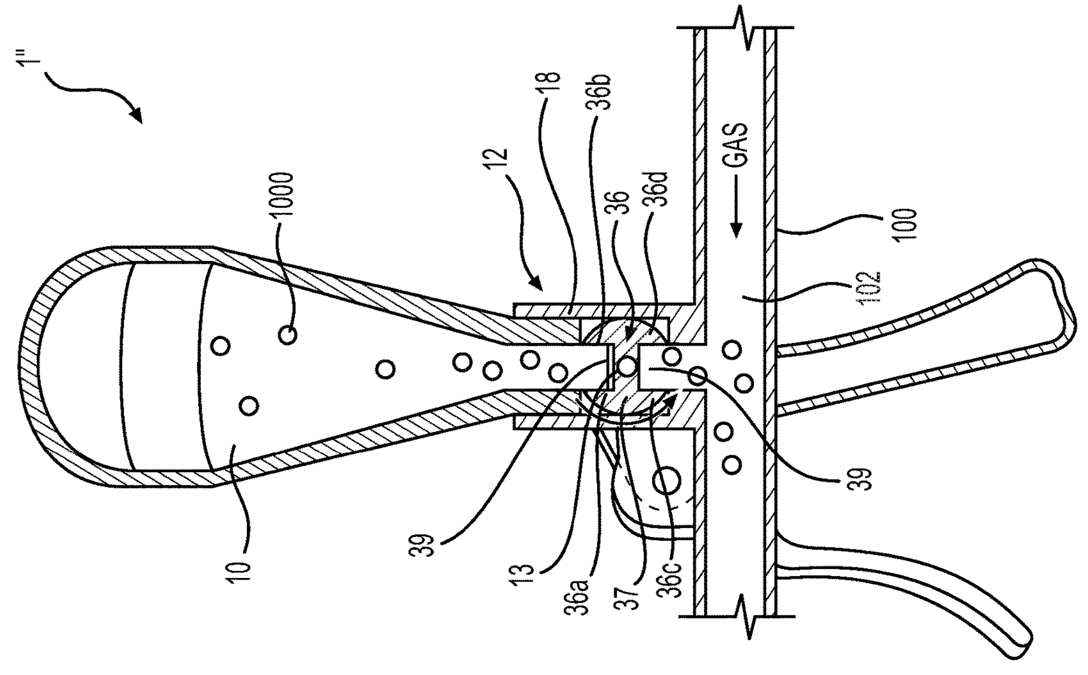
FIG. 3A is a cross-sectional view of a medical device, according to another embodiment.

Medical device 1", as shown in FIG. 3A, is similar to device 1 in many respects. Like reference numerals refer to like parts. Differences between device 1 and device 1" will be described below. Device 1" includes a rotatable ball valve 36 as the dosing mechanism. However, valve 36 is not limited to being a ball-shape, and may be other suitable shapes. Valve 36 includes rotational axis 13, which is aligned with the diameter of ball valve 36 that is perpendicular to the width of channel 12. Valve 36 further includes two pairs of prongs, 36*a*-36*b* and 36*c*-36*d*, that are diametrically opposed, across axis 13. In other embodiments, valve 36 may have only one pair of prongs or additional pairs of prongs. The void between the prongs in each pair forms a bucket 39 configured to receive and store agent 1000. Thus, valve 36 includes two buckets 39 up to approximately 180° apart. However, valve 36 is not limited to two buckets 39, as previously described, and in some embodiments may have one bucket 39 or additional buckets 39, spaced at any desired interval about valve 36. Furthermore, the two dome-shaped portions of valve 36 between diametrically opposed prongs, e.g., 36*a* and 36*c*, 36*b* and 36*d*, form flanges 37. Ball valve 36 may be of a diameter so that at least some portion of valve 36 is in constant, or near constant, contact with seals 18 or, in embodiments without seals, the inner surfaces of channel 12. Valve 36 may be of any suitable material. Thus, valve 36 may serve as a barrier between lumen 102 and enclosure 10, thereby inhibiting fluid, e.g., gas, from undesirably mixing with the contents of enclosure 10.

The openings of buckets 39, that are to be in connection with channel 12, are of a width that is at least equal to the width of an opening of channel 12 leading to valve 36. Thus, all of agent 1000 from enclosure 10 traveling through channel 12 is received within buckets 39, without any agent 1000 falling outside of buckets 39. Buckets 39 may be sized appropriately so that a number of buckets 39, e.g., one or two, is an appropriate dosage of agent 1000. The dimensions of buckets 39 may also be tailored to meet a predefined, predetermined or selected dose per rotation or a number of rotations. For example, an appropriate dose range may be between about 0.1 to 1 g of agent 1000, or about 0.2 to 0.5 g of agent 1000, for every second of fluid delivery in lumen 102. Flanges 37 are of a width that sufficiently covers and seals channel 12 as flanges 37 rotationally pass by the proximal and distal openings of channel 12. As a result, flanges 37 inhibit additional or excess agent 1000 from falling from enclosure 10 to lumen 102.

Seals 18" may be similar to seals 18 in some respects. For example, the inner surfaces of seals 18" may be curved to accommodate for the spherical shape of ball valve 36. Seals 18" are positioned to partially or fully surround valve 36 and to provide a seal around channel 12 so that agent 1000 is inhibited from falling anywhere outside of buckets 39, and fluid (e.g., $CO_2$) is inhibited from entering enclosure 10. Thus, seals 18" inhibit agent 1000 from falling unimpeded into lumen 102 without passing through valve 36, and also inhibit agent 1000 from spilling out of buckets 39 prior to the intended agent-dispensing period.

Referring to FIG. 3B, a mechanical mechanism of medical device 1", by which valve 36 rotates, is further described below. Valve 36 rotates via a mechanism including a handle 31, a lever 32, a pivot 33, and an axis gear 35. Handle 31 is fixed relative to enclosure 10, channel 12, and tube 100. Handle 31 is not particularly limited, and may include any suitable handle grip 31*a*. Handle 31 further includes a flat, triangular head 31*b*, which includes two openings-one on a distal portion of head 31*b* and the other on a relatively proximal portion of head 31*b*. Said proximal opening accommodates rotational axis 13. Handle 31 remains stationary about axis 13, but axis 13 may rotate within head 31*b* via a rotational force exerted thereon. Axis gear 35 is coupled onto the end portion of rotational axis 13 protruding out of said proximal opening on head 31*b*. Axis gear 35 may be coupled onto rotational axis 13 so that rotation of gear 35 may cause simultaneous rotation of axis 13, which in turn rotates valve 36 (see FIG. 3A; note that FIG. 3B does not show valve 36, so that axis 13 can be shown). Lever 32 includes a handle portion 32*a* and a head portion 32*b*. Handle portion 32*a* is not particularly limited. Head 32*b* includes a plurality of teeth 34, which are engage with axis gear 35. Head 32*b* also includes an opening that is to be aligned with an opening of the handle head 31*b*. Pivot 33 may be any suitable pivot, and is positioned in the aligned openings so that pivot 33 pivotably couples lever head 32*b* to handle head 31*b*. Furthermore, pivot 33 may also be spring-loaded (not shown), so that lever 32 may revert to its original position after pivoting towards handle 31.

Medical device 1" may be used in a similar manner as medical device 1, except a user actuates lever 32, e.g., pivoting lever 32 towards handle 31. This causes head 32*b* to rotate about pivot 33. This, in turn, causes the plurality of teeth 34 engaged with axis gear 35 to rotate axis gear 35 by a predetermined or selected degree, e.g., 180°, thereby rotating valve 36 per each pump of lever 32. The rotation of valve 36 may proceed in a single direction (clockwise or counter-clockwise 180°), or alternate clockwise and counter-clockwise 180°, via each actuation and subsequent release of lever 32). In exemplary embodiments, in which rotation of valve 36 proceeds in a single direction, any suitable ratcheting mechanism may be employed to limit the rotary motion of valve 36 to only one direction. In other examples, the above-described mechanism may further include a motor in connection with gear 35 and lever 32, along with any other additional components, so that a mechanism may be configured to result in continuous rotation of axis gear 35 and valve 36 by a pull of lever 32, until lever 32 is released.

However, it is noted that medical device 1" is not limited to the above-described configuration. For example, in some embodiments, valve 36 may be in lumen 102, directly below channel 12. In such a configuration, there may be fluid communication from enclosure 10 to bucket 39, via channel 12. Valve 36, after one of buckets 39 is loaded, may only need to rotate 90° (or about 90°) counter-clockwise, to dispense agent 1000 from one of buckets 39 to lumen 102. Furthermore, in this configuration, valve 36 or lumen 102 may include additional means by which the fluid stream, from a proximal end of lumen 102, may reach the dispensed agent 1000 and propel agent 1000 towards a distal end of lumen 102. For example, lumen 102 may have a diameter that is large enough to accommodate both valve 36 and a gap between valve 36 and an inner surface of tube 100 for air/pressurized fluid to flow through. For example, valve 36 may be placed within lumen 102 so that valve 36 is adjacent to and just below the exit of channel 12 (i.e., the opening of channel 12 nearest lumen 102), and air may flow underneath valve 36 via the aforementioned gap. Thus, the air may propel agent 1000 towards a distal end of lumen 102 as soon as loaded valve 36 rotates counter-clockwise to dispense agent 1000. In another example, valve 36 may further include a passage, which may be substantially parallel to a longitudinal axis of buckets 39, and which may extend between buckets 39 (from a radially inner edge of one bucket 39 to a radially inner edge of the other bucket 39). A porous structure, e.g., a screen/filter, may be disposed within the passage. Alternatively, a body of valve 36 itself may define a porous structure, such that a separate screen/filter is not required. The passage may be misaligned from the air/pressurized fluid flow, such that the air/pressurized fluid flow may not enter the passage, while one of buckets 39 is loaded with agent 1000. When valve 36 rotates 90° (or about 90°) to dispense agent 1000, air/pressurized fluid may flow through buckets 39 and the passage of valve 36 to propel agent 1000 distally. The opening(s) of the porous structure, e.g., screen/filter, should be small enough so that agent 1000 remains contained in buckets 39, without falling through the opening(s) into the passage, while one of the buckets 39 is loaded with agent 1000. In an alternative, valve 36 may include only one bucket 39, and the passage may terminate at one end in an opening in a surface of valve 36, opposite bucket 39. In other exemplary embodiments, medical device 1" may be without channel 12, so that enclosure 10 is adjacently above valve 36 (in lumen 102).

Additional examples of different medical device 1"*a-d* configurations are illustrated in FIGS. 3C-3J, and are further described below. It is noted that all the configurations described below may rotate via any suitable mechanism, including the gearing mechanism shown in FIG. 3B or suitable variations thereof.

Figure 3D:
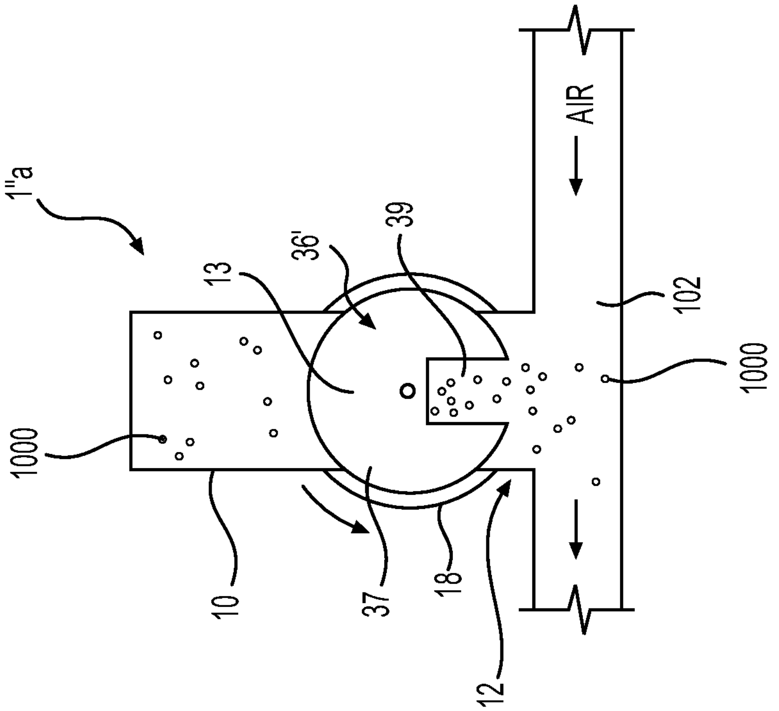
FIGS. 3C-3J are cross-sectional views of various ball-valve configurations within medical devices, according to other embodiments.
Figure 3C:
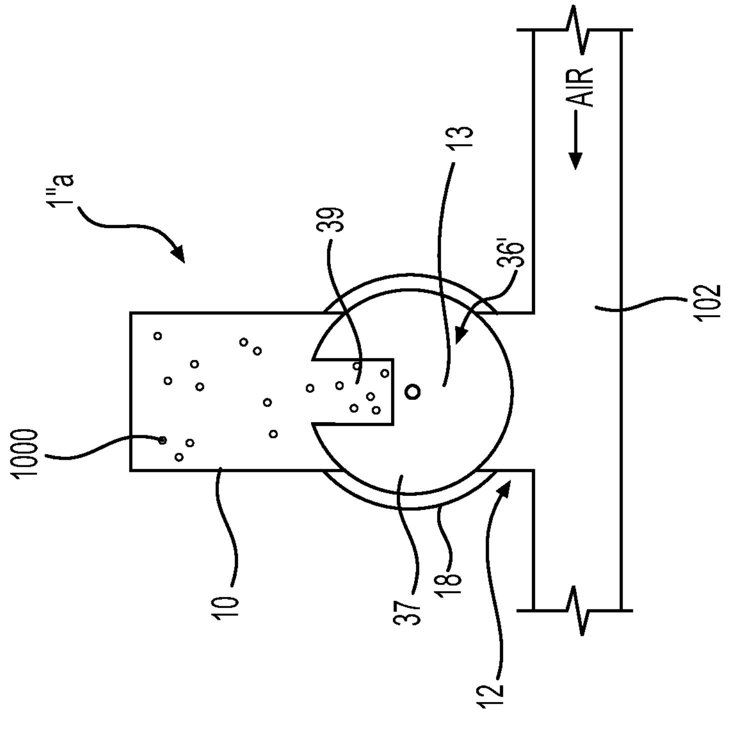

FIGS. 3C-3D illustrate a configuration 1"*a* similar to medical device 1" shown in FIG. 3A, except valve 36' has only one bucket 39 to receive and store agent 1000. FIG. 3C shows a closed position of configuration 1"*a* in which bucket 39 is filled with agent 1000 and flange 37 seals enclosure 10 from lumen 102. FIG. 3D shows an open position in which valve 36' is rotated 180° so that bucket 39 faces lumen 102, thereby dispensing agent 1000 into lumen 102.

Figure 3F:
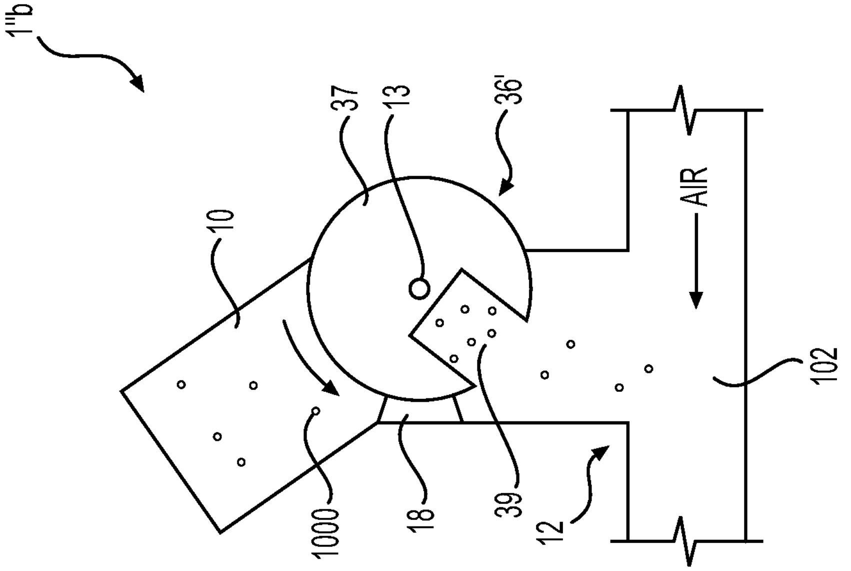
Figure 3E:
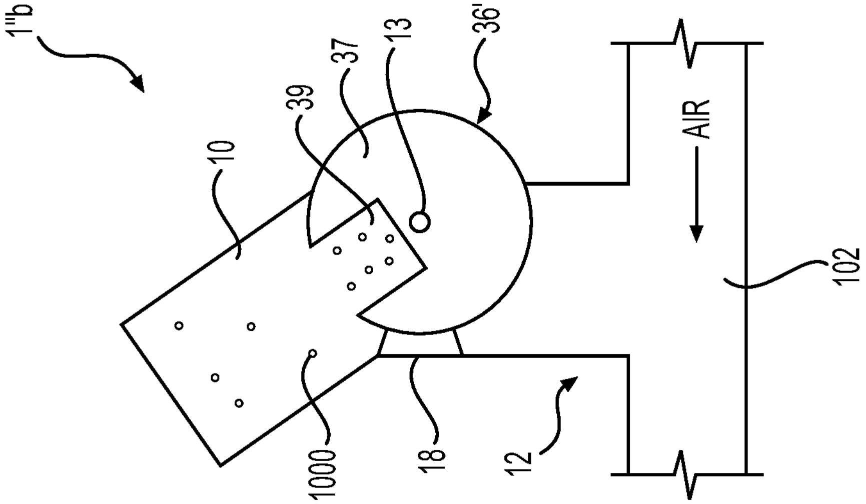

FIGS. 3E-3F illustrate a configuration 1"*b* in which enclosure 10 and valve 36' are oriented at an angle relative to channel 12 and lumen 102. The central axis of enclosure 10 is transverse to the central axis of channel 12. Configuration 1"*b* further includes a seal 18 that is positioned between enclosure 10 and channel 12. Due to seal 18, agent 1000 is inhibited from directly falling out from enclosure 10 to channel 12. Furthermore, agent 1000 is also inhibited from spilling out of bucket 39 as valve 36' rotates to dispense agent 1000 from bucket 39 to lumen 102. FIG. 3E shows a closed position of configuration 1"*b* similar to that shown in FIG. 3C. FIG. 3F shows an open position in which valve 36' is rotated 90° counter-clockwise, so that bucket 39 faces channel 12, thereby dispense agent 1000 into lumen 102. Thus, compared to some other embodiments, less rotation of valve 36' is needed in configuration 1"*b* to release agent 1000 from bucket 39.

Figure 3H:
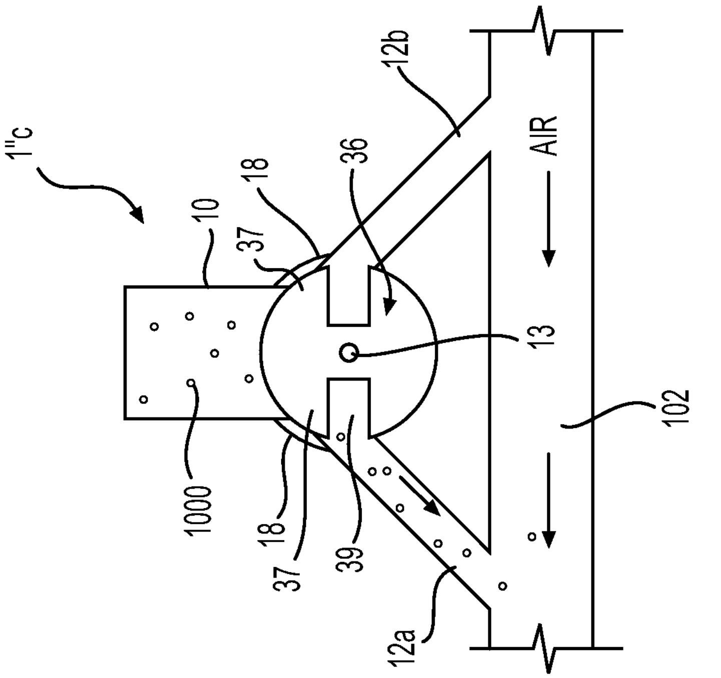
Figure 3G:
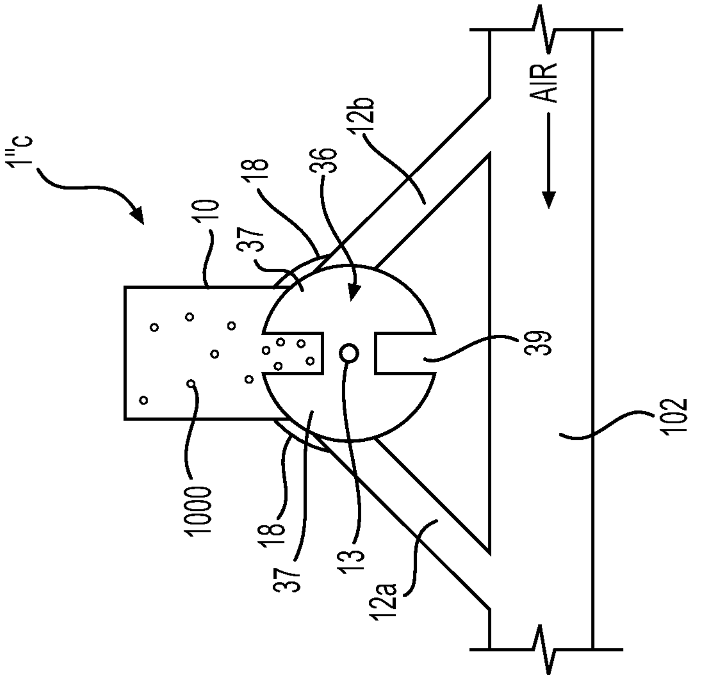

FIGS. 3G-3H illustrate a configuration 1"*c* similar to medical device 1" shown in FIG. 3A, except configuration 1"*c* includes a first channel 12*a* and a second channel 12*b*. First channel 12*a* and second channel 12*b* are linear (though they may be curved) and are positioned so that fluid communication between both buckets 39 and lumen 102 may be established when valve 36 is rotated. Channel 12*a* is distal to valve 36 while channel 12*b* is proximal to valve 36. The central axes of channels 12*a* and 12*b* are transverse to the central axis of enclosure 10 and the axes of lumen 102. The angle at which channel 12*a* connects to lumen 102 is equivalent to or about equivalent to the angle at which channel 12*b* connects to lumen 102, though this is not required. It is noted that agent 1000 may dispense into channel 12*a* or channel 12*b* depending on the counterclockwise or clockwise rotation of valve 36 respectively. The incorporation of two channels 12*a* and 12*b* also allows device 1" to continue to function in the chance that one of channels 12*a* or 12*b* clogs, rotation of valve 36 is inhibited in one of the directions, or some other malfunction prevents use of one of the channels 12*a*, 12*b*. Configuration 1"*c* further includes seals 18 that are positioned between enclosure 10 and channel 12*a* and enclosure 10 and channel 12*b*. Due to such placement of seals 18, agent 1000 is inhibited from spilling out of buckets 39 as valve 36 rotates to dispense agent 1000 from bucket 19 to channel 12*a* or channel 12*b*. FIG. 3G shows a closed position of configuration 1"*c* similar to that shown in FIG. 3C. FIG. 3H shows an open position in which valve 36 is rotated 90° counter-clockwise, so that agent 1000 from loaded bucket 19 is dispensed into first channel 12*a*. Alternatively, in some instances, valve 36 may rotate 90° clockwise so that agent 1000 from loaded bucket 39 is dispensed into second channel 12*b*. Thus, similar to configuration 1"*b*, less rotation of valve 36' is needed in configuration 1"*c*, compared to some other embodiments, to release agent 1000 from bucket 39 into channel 12*a* or 12*b*.

Figure 3J:
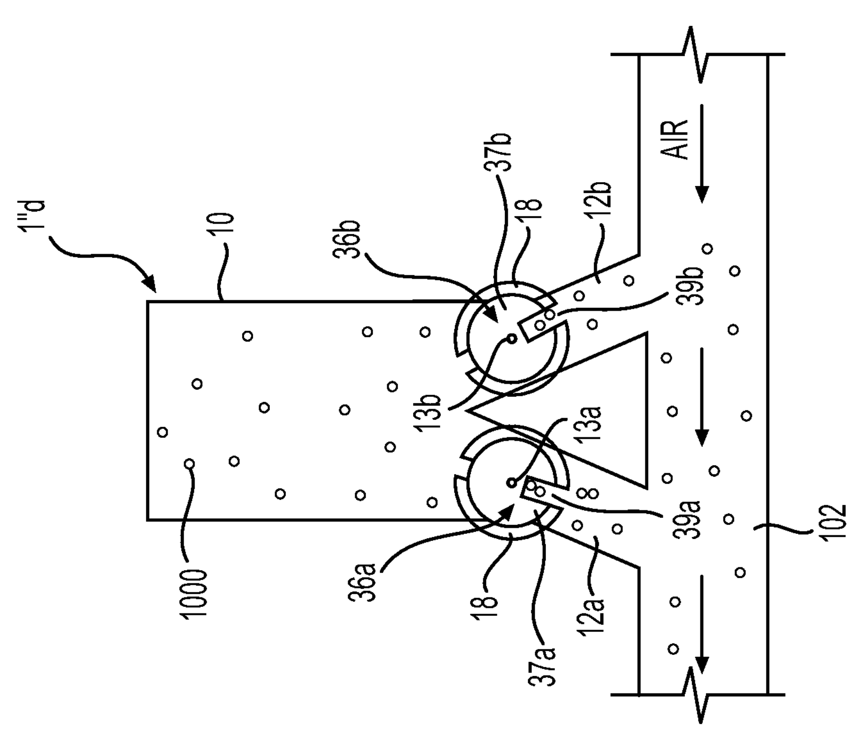
Figure 3I:
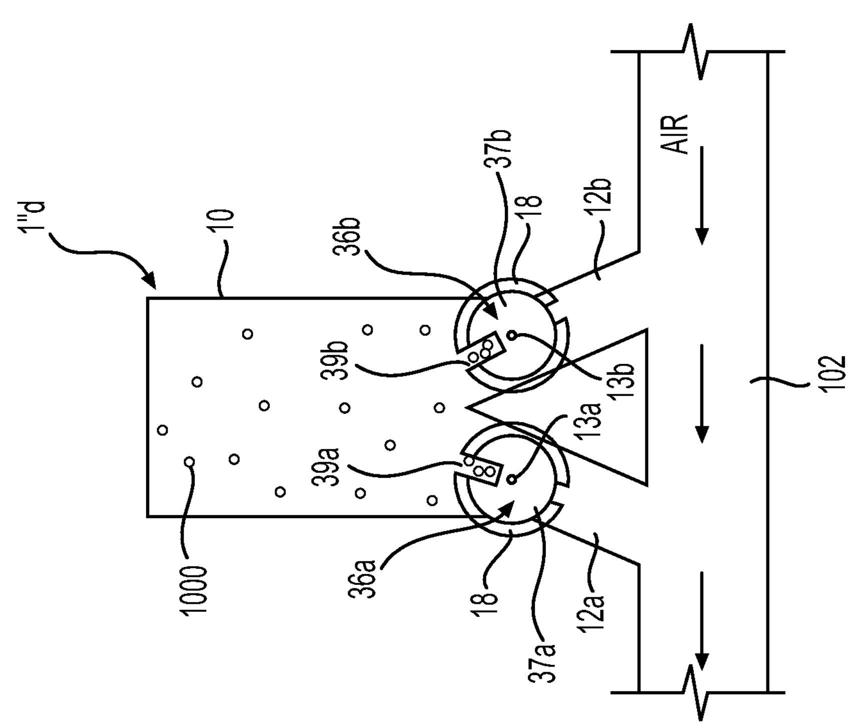

FIGS. 3I-3J illustrate a configuration 1"*d* similar to configuration 1"*a* shown in FIG. 3C, except configuration 1"*d* includes a first channel 12*a* and a second channel 12*b* (like configuration 1"*c*), and a first valve 36'*a* and a second valve 36'*b* corresponding to each channel 12*a*, 12*b* respectively. First channel 12*a* and second channel 12*b* are linear (like configuration 1"*c*) (though they may be curved), and the central axis of channels 12*a* and 12*b* are transverse to the central axis of enclosure 10 and the axes of lumen 102. Channel 12*a* is distal relative to channel 12*b*, and likewise, channel 12*a* leads to a more distal portion of lumen 102 than does channel 12*b*. Channels 12*a* and 12*b* are angled relative to enclosure 10 (like channels 12*a*, 12*b*, in FIGS. 3G-3H) so that a triangular gap is formed in between channels 12*a*, 12*b*, and lumen 100. The angle at which channel 12*a* connects to lumen 102 is equivalent to or about equivalent to the angle at which channel 12*b* connects to lumen 102, though this is not required. First valve 36'*a* and a second valve 36'*b* are respectively positioned within channels 12*a* and 12*b*, similar to configuration 1"*a*. Because of the presence of two, separate valves, 36'*a* and 36'*b*, agent 1000 may be dispensed simultaneously via channels 12*a* and 12*b*. This configuration may also provide for a more careful dosage means by allowing independent actuation of only one of the valves. Configuration 1"*d* further includes seals 18 partially surrounding both first valve 36'*a* and second valve 36'*b*. FIG. 3I shows a closed position similar to that shown in FIG. 3C. FIG. 3J shows an open position in which valves 36'*a* and 36'*b* are simultaneously or sequentially rotated 180°, so that buckets 39*a* and 39*b* face channels 12*a* and 12*b*, thereby dispense agent 1000 into lumen 102.

Figure 4:
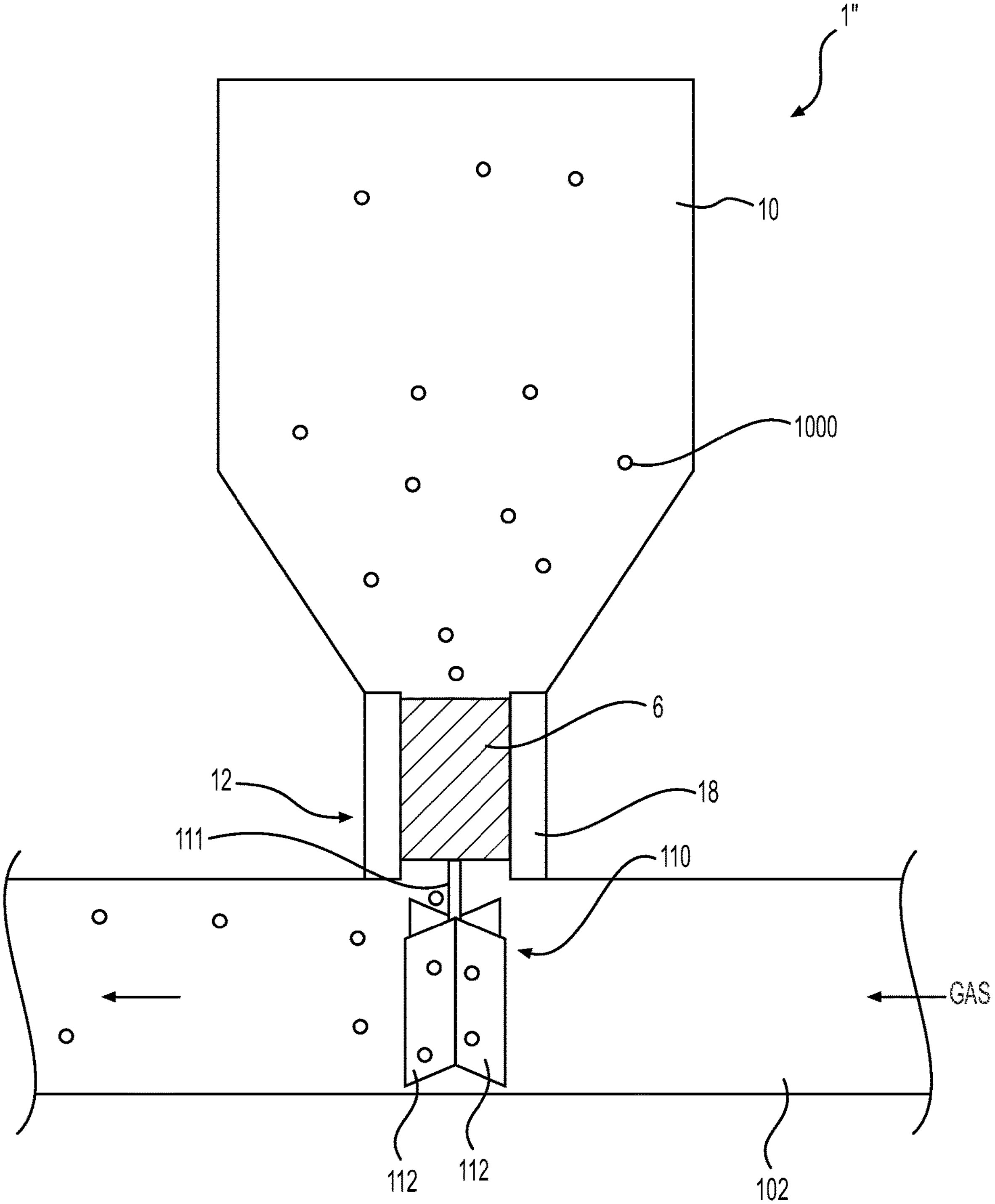
FIG. 4 is a cross-sectional view of a portion of a medical device, according to another embodiment.

FIG. 4 illustrates a medical device 1''' that is similar in many respects devices 1, 1', 1" described above. Like reference numerals refer to like parts. Medical device 1''' includes a general dosing mechanism 6. Dosing mechanism 6 is not particularly limited, and may include rotational dosing mechanisms, e.g., wheel 16, auger 26, valve 36, or other dosing mechanisms. Medical device 1''' further includes a turbine 110 including a rotational axis 111 and panels 112. Turbine 110 is positioned within lumen 102 so that it is in line with the fluid stream, which assists in the rotation of turbine 110. Rotational axis 111 may be fixedly coupled to dosing mechanism 6 so that rotation of axis 111 rotates dosing mechanism 6 about axis 111 and also about a central axis of channel 12. Panels 112 are rectangular in shape and extend radially outward from axis 111. However, the shape of panels 112, as well as the number of panels 112 (four shown in FIG. 4), is not particularly limited. Panels 112 are equally spaced apart around axis 111, but may be spaced at unequal intervals. Thus, rotation of turbine 110, via the fluid stream pushing against panels 112, rotates axis 111, which, in turn, rotates dosing mechanism, thereby dispensing agent 1000. Thus, in this embodiment, the fluid stream from lumen 102 may be used to actuate dispensing of agent 1000, and there may be no need for a separate actuation for rotating dosing mechanism 6. Furthermore, this embodiment ensures a constant fluid stream during the dispensing of agent 1000.

FIG. 5 illustrates a hydraulic system 200. Hydraulic system 200 is not limited to a particular function for the above-mentioned medical device embodiments. Rather, system 200 may be implemented as a driving mechanism that may be used for any function of medical device 1, 1', 1" requiring a drive mechanism, e.g., rotation of wheel 16 or auger 26. Hydraulic system 200 includes a piston 201, a spring 202, a liquid reservoir 204 housing a first plunger 203, and a channel 205 leading out of reservoir 204. Channel 205 includes a valve 206 and a restrictor 207 along its path, and leading into a syringe 208.

Piston 201 is not particularly limited, and may be any suitable piston, for example, a cylindrical rod, configured to linearly drive towards and retract from first plunger 203. Spring 202, likewise, is not particularly limited, and may be any suitable spring. Spring 202 is coupled to one end of piston 201 and an adjacent surface of plunger 203, so that spring 202 is positioned between piston 201 and plunger 203. Liquid reservoir 204, which is pre-filled with a liquid, e.g., water, is of a width equal to that of plunger 203, so that plunger 203 may move linearly within reservoir 204 from one end to the other. Plunger 203 may include a seal about its circumference to seal against a wall of reservoir 204, so that liquid does not leak around plunger 203. The drive of piston 201 may compress spring 202, thereby causing plunger 203 to advance linearly, via the spring force of compressed spring 202, and pushing the liquid towards channel 205. Channel 205 is of a smaller width/diameter than reservoir 204, and includes a valve 206, that is positioned between a first portion 205*a* and a second portion 205*b* of channel 205. Valve 206 may be any suitable valve that may be actuated to open/close to permit/restrict the passage of liquid through channel 205. Restrictor 207, positioned in the second portion 205*b* of channel 205, includes an orifice which controls the rate of liquid flowing through restrictor 207. The means by which restrictor 207 controls flow rate of the liquid into syringe 208 is not particularly limited, and may be by any suitable means. Syringe 208 is connected to the end of channel 205 on one side, thereby establishing fluid communication between syringe 208 and reservoir 204 (when valve 206 is opened). Syringe 208 houses a second plunger 209 configured to move linearly from one end to the other end of syringe 208, e.g., the first channel side to the second channel side. Plunger 209 may have the same width/diameter as syringe 208 so that plunger 209 may move linearly within syringe 208. Plunger 209 may also include a seal about its circumference to seal against an inner wall of syringe 208, so that liquid does not leak around plunger 209. The flow of liquid from reservoir 204 to syringe 208 pushes on plunger 209 so that plunger 209 may advance linearly. Plunger 209 may be coupled to the above-described medical devices by any suitable means, and may serve as a driving mechanism for actuating various functions of said medical devices. For example, the linear drive of plunger 209 may cause rotation of a gear that results in rotation of a metering/dosing mechanism, e.g., wheel 16, auger 26, or may mechanically push agent 1000 towards the metering/dosing mechanisms of medical devices.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:

an enclosure defining a cavity for containing an agent;

a lumen for receiving a pressurized fluid;

a channel between the cavity and the lumen; and a barrier positioned in the lumen and below the channel, the barrier including a pair of openings and a passage extending between the pair of openings, the passage and the pair of openings defining a space extending through the barrier, wherein in a first position of the barrier, the space is in fluid communication with the cavity and the lumen to receive and deliver the agent from the cavity to the lumen, and wherein the barrier is configured to rotate from the first position to a second position in which the space is not in fluid communication with the cavity; and wherein the barrier includes a diameter less than an interior diameter of the lumen, and a gap is formed between an interior of the lumen and an exterior of the barrier such that, in the second position of the barrier, the barrier is configured such that a first portion of the pressurized fluid in the lumen travels around the barrier and through the gap while the space is configured to simultaneously receive a second portion of the pressurized fluid through the pair of openings and the passage to mix with the agent stored therein, thereby combining the pressurized fluid and the agent within the lumen.

2. The medical device of claim 1, wherein, in the second position, the barrier seals the cavity from the lumen, inhibiting the pressurized fluid of the lumen from entering into the cavity.

3. The medical device of claim 1, further comprising at least one seal defining at least a portion of the channel, wherein the at least one seal contacts the barrier to inhibit the agent from entering the lumen without entering the space, and to inhibit the agent from exiting the space when the barrier is in the second position.

4. The medical device of claim 1, further comprising a second channel between the cavity and the lumen.

5. The medical device of claim 4, further comprising a second barrier positioned in the second channel and defining a second barrier space, wherein in a first position of the second barrier, the second barrier space is in fluid communication with the cavity to receive the agent from the cavity, and wherein the second barrier is configured to rotate from the first position to a second position in which the second barrier space is in fluid communication with the lumen to deliver the agent from the second barrier space to the lumen.

6. The medical device of claim 1, further comprising a turbine positioned within the lumen so that the pressurized fluid rotates the turbine, and rotation of the turbine rotates the barrier from the first position to the second position.

7. The medical device of claim 1, wherein the barrier is a ball valve, wherein the ball valve includes at least one pair of prongs and a gap between the prongs defines at least one of the pair of openings.

8. The medical device of claim 7, wherein the at least one pair of prongs includes first and second pairs of prongs diametrically opposed across the ball valve, and the gap between the prongs in the first pair of prongs defines a first space, and the gap between the prongs in the second pair of prongs defines a second space.

9. The medical device of claim 1, wherein a rotation of the barrier is actuated by a mechanical system or a hydraulic system associated with the medical device.

10. The medical device of claim 1, wherein the lumen is a flexible catheter capable of traversing a tortuous body lumen, and further comprising a source of the pressurized fluid.

11. The medical device of claim 1, wherein the barrier is configured to rotate from the first position to the second position via both clockwise rotation and counterclockwise rotation.

12. The medical device of claim 1, wherein the barrier is configured to rotate at least one of 90° or 180°, to transition from the first position to the second position.

13. The medical device of claim 1, wherein the pair of openings are positioned on opposing sides of the barrier, and the passage extends parallel to a longitudinal axis of each of the pair of openings.

14. The medical device of claim 1, further comprising a porous filter disposed within the barrier, the porous filter being configured to inhibit the agent from flowing in a direction opposite to the pressurized fluid and allow the pressurized fluid to flow through the barrier, such that the agent remains contained within the barrier for mixing with second portion of the pressurized fluid.

15. The medical device of claim 1, wherein the enclosure includes a bottom portion that is tapered radially-inwards such that the cavity funnels the agent radially-inwards towards at least one of the pair of openings of the barrier.

16. A medical device, comprising:

an enclosure defining a cavity for containing an agent;

a lumen for receiving a pressurized fluid; and a barrier including a pair of openings and a passage between the pair of openings for collectively defining a space through the barrier, and the barrier is configured to be positioned relative to the enclosure and the lumen to selectively allow and inhibit fluid communication between the cavity and the lumen, the barrier includes a diameter less than an interior diameter of the lumen, thereby forming a gap between an interior of the lumen and an exterior of the barrier, and wherein in a first position of the barrier, the space is in fluid communication with the cavity and the lumen to receive and deliver the agent from the cavity to the lumen, and wherein the barrier is configured to rotate from the first position to a second position in which the space is not in fluid communication with the cavity; and wherein in the second position of the barrier, the barrier is configured to form the gap between the interior of the lumen and the exterior of the barrier to receive a first portion of the pressurized fluid as the barrier inhibits delivery of the agent from the cavity to the lumen, and the space is configured to simultaneously receive a second portion of the pressurized fluid through the pair of openings to mix with the agent stored in the passage, thereby combining the pressurized fluid and the agent within the lumen.

17. The medical device of claim 16, wherein the barrier is a ball valve, wherein the ball valve includes at least one pair of prongs and a gap between the prongs defines the space.

18. The medical device of claim 17, wherein the ball valve is positioned in the lumen below the cavity, and wherein the ball valve is configured to rotate counterclockwise to rotate from the first position to the second position.

19. The medical device of claim 18, wherein the barrier is configured to rotate 90° to transition from the first position to the second position.

20. A medical device, comprising:

an enclosure containing an agent;

a lumen for receiving a pressurized fluid; and a barrier positioned in the lumen and below the enclosure, the barrier including a pair of openings and a passage extending between the pair of openings, the barrier is configured to move relative to the enclosure and the lumen to selectively mix the agent from the enclosure with the pressurized fluid from the lumen, wherein the barrier includes a diameter less than an interior diameter of the lumen, thereby forming a gap between an interior of the lumen and an exterior of the barrier;

wherein, in a first position, the pair of openings are aligned with the enclosure and the lumen such that the passage is in fluid communication with the agent and the pressurized fluid, thereby receiving the agent through the barrier for mixing with the pressurized fluid; and wherein, in a second position, the pair of openings are misaligned with the enclosure such that the passage is not in fluid communication with the enclosure, and the gap formed between the interior of the lumen and the exterior of the barrier remains in fluid communication with the pressurized fluid such that a first portion of the pressurized fluid is directed around the barrier and through the gap while the barrier is configured to simultaneously receive a second portion of the pressurized fluid through the pair of to mix with the agent stored in the passage, thereby combining the pressurized fluid and the agent within the lumen for delivery from the medical device.

* * * * *